United States Patent [19]

D'Silva

[11] Patent Number: 4,988,069
[45] Date of Patent: Jan. 29, 1991

[54] STEPPING MOTOR MOUNTING

[75] Inventor: Edmund D. D'Silva, Highland Park, Ill.

[73] Assignee: Baxter International Inc., Deerfield, Ill.

[21] Appl. No.: 441,852

[22] Filed: Nov. 27, 1989

[51] Int. Cl.5 .................................................. F04B 21/00
[52] U.S. Cl. ....................................... 248/605; 248/638; 417/474; 417/363
[58] Field of Search ............... 248/618, 619, 620, 636, 248/638, 605; 310/51, 91; 417/474, 363

[56] References Cited

U.S. PATENT DOCUMENTS

| | | | |
|---|---|---|---|
| 1,998,338 | 4/1935 | Spohrer | 417/363 |
| 2,349,845 | 5/1944 | Cody | 417/363 |
| 2,637,514 | 5/1953 | O'Connor | 248/605 |
| 3,726,613 | 4/1973 | von Casimir | 417/477 |
| 4,373,525 | 2/1983 | Kobayashi | 128/214 |
| 4,482,347 | 11/1984 | Borsanyi | 604/153 |
| 4,488,700 | 12/1984 | Nakamura | 310/51 |
| 4,493,706 | 1/1985 | Borsanyi et al. | 604/153 |
| 4,561,830 | 12/1985 | Bradley | 417/474 |
| 4,648,812 | 3/1987 | Kobayashi et al. | 417/477 |
| 4,671,792 | 6/1987 | Borsanyi | 604/153 |
| 4,725,205 | 2/1988 | Cannon | 417/474 |
| 4,728,265 | 3/1988 | Cannon | 417/363 |
| 4,869,646 | 9/1989 | Gordon | 417/474 |

FOREIGN PATENT DOCUMENTS

| | | | |
|---|---|---|---|
| 169117 | 9/1921 | United Kingdom | 248/605 |
| 413092 | 7/1934 | United Kingdom | 248/605 |

Primary Examiner—Ramon O. Ramirez
Assistant Examiner—Robert A. Olson
Attorney, Agent, or Firm—Paul E. Schaafsma; Paul C. Flattery; Brandford R. L. Price

[57] ABSTRACT

A mounting for a stepping motor (42) in a peristaltic pump (20) is provided. The mounting includes a first bracket (81) which rigidly scures stepping motor housing (58) in a radial direction while providing a bearing assembly (96) connecting the first bracket (81) and the stepping motor housing (58) to allow for free rotational movement. A second bracket (62) is also secured to the stepping motor housing (58) which includes at least one spring (72) which dampens tangential forces.

15 Claims, 4 Drawing Sheets

STEPPING MOTOR MOUNTING

FIELD OF THE INVENTION

The present invention relates in general to peristaltic pumps and in particular to a mounting for stepping motors utilized in peristaltic pumps.

BACKGROUND OF THE INVENTION

Administration of intravenous fluids to a patient is well known in the art. Typically, a solution such as saline, glucose or electrolyte in a glass or flexible container is fed to a patient's venous access site via a length of flexible plastic tubing such as polyvinyl chloride (PVC) tubing. The rate of flow of the fluid is controlled by a roller clamp which is adjusted to restrict the flow lumen of the tubing until the desired flow rate is obtained.

Flow from the container to the patient may also be regulated by means other than a roller clamp. It is becoming more and more common to use an electronically controlled pump. One type of pump that is used for intravenous fluid administration is a peristaltic-type pump.

Use of peristaltic pumping action is particularly well suited for the medical field. This is because peristaltic pumping action can be applied externally of the tubing carrying the intravenous fluid. This maintains the sterile condition of the intravenous fluid within the tubing while imparting fluid propulsion on the fluid. The peristaltic pumping action can also be applied at any point on the tubing.

In a common type of peristaltic pump used in the medical field, a driving motor is connected to an array of cams angularly spaced from each other. The cams in turn drive cam followers which are connected to corresponding pressure fingers. These elements cooperate to impart a linear wave motion on the pressure fingers. A pressure plate is secured juxtaposed to and spaced from the pressure fingers. The pressure plate holds the tubing against the reciprocating pressure fingers to impart the wave motion on the tubing to propel the fluid.

In a preferred embodiment of peristaltic pumps, the driving motor is a stepping motor which rotates in small increments or steps. While a stepping motor rotating at a high rate of speed gives a visual impression that the rotation is constant, the stepping motor in fact turns through a series of small angular increments or steps which are followed by brief periods of rest. In stepping motors utilized in peristaltic pumps in the medical field, these small angular steps can range from about 0.36° to 7.2° and in a preferred embodiment are about 1.8°. This results in a series of steps of the shaft between 1000 and 50 per revolution or, in the preferred embodiment, about 200 steps per revolution.

The stepping motors utilized in peristaltic pumps effectively drive the peristaltic pumping action. However, the stepping action of the pumps can result in excessive vibration which results in a loud chattering or buzzing noise as a result of amplification by the pump housing.

Various solutions have been proposed to reduce this vibration noise. Traditional shock mounts which consist of four springs connecting the pump housing and the motor frame have been used. These shock mounts, however are designed to absorb and dampen radial vibrations caused by imbalanced forces on the motor shaft and thus do not efficiently dampen the tangential forces generated in the stepping motor.

While "softer" shock absorption can be utilized to eliminate the vibrations and noise, such soft absorption detracts from the accuracy of the stepping motor and presents reliability problems as a result of the soft mounting of the stepping motor to the pump housing.

Another proposed solution is to couple the stepping motor shaft to the cams with a shock absorbing coupler. This solution, however, also suffers from the problem of accuracy and reliability if sufficient absorption is provided to quiet the stepping noise.

What is thus needed is a device which sufficiently absorbs the forces transmitted by the stepping motor to reduce the stepping vibration and noise while maintaining a high degree of accuracy and reliability. The present invention provides such a device.

SUMMARY OF THE INVENTION

The present invention provides an improved mounting for stepping motors in peristaltic pumps which maintains accurate infusion while reducing the vibration and noise of the stepping movement. A first bracket is provided which allows slight rotational movement of the driving motor frame while providing rigid radial support. A second bracket is provided which dampens tangential forces to reduce the vibration and noise of the stepping movement.

The first bracket includes bearing housing connecting the driving motor to pump housing. The bearing housing provides rigid radial support while allowing for free rotational movement of the driving motor. The second bracket provides at least one biasing member connecting the second bracket to the pump housing. The biasing member dampens the tangential forces exerted on the motor housing by the stepping movement of the motor. In a preferred embodiment, the biasing member is oriented along a tangential plane extending from this axis of rotation of the stepping motor to further dampen the tangential forces of the stepping motor.

DETAILED DESCRIPTION OF A PREFERRED EMBODIMENT

Figure 1:
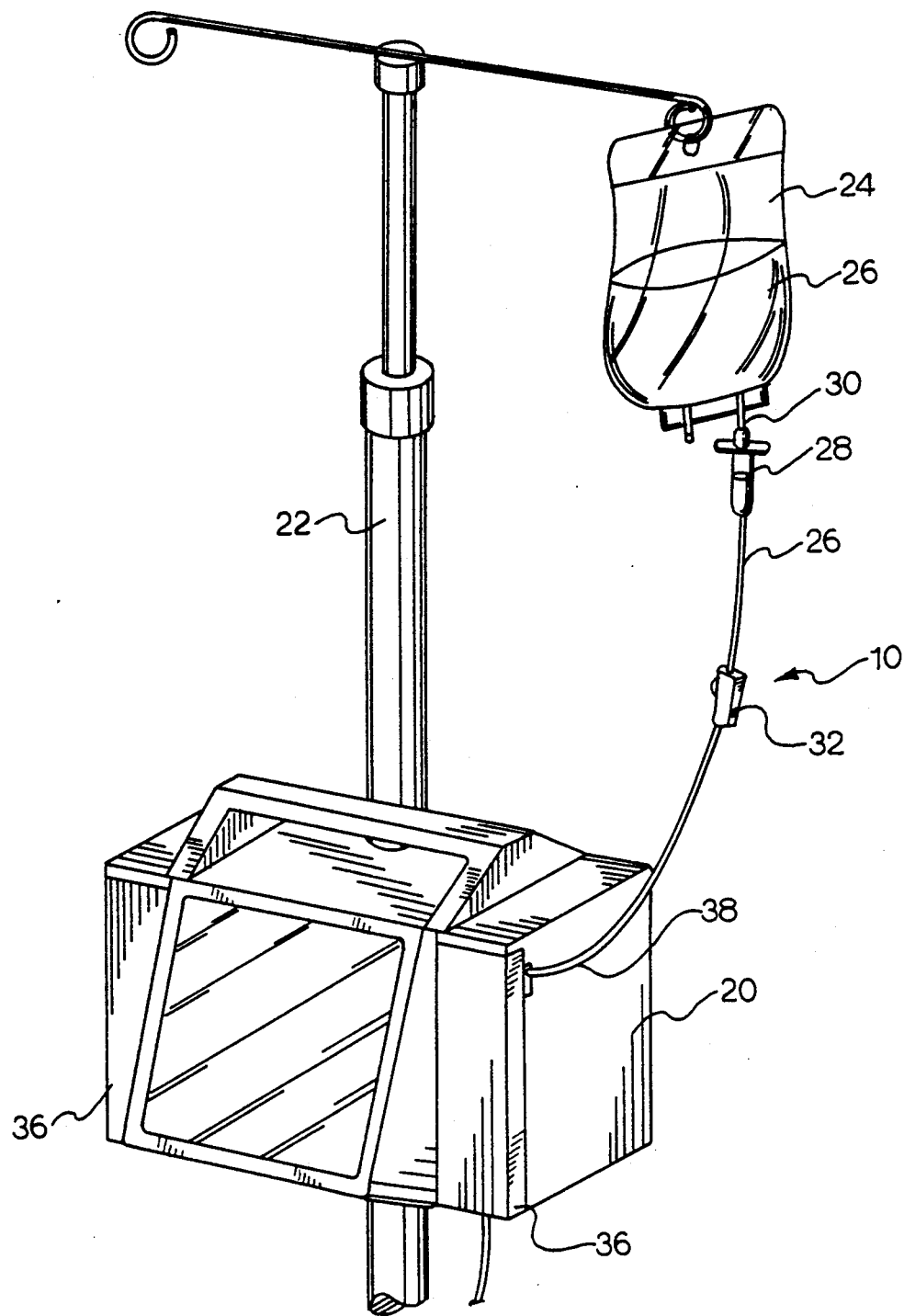
FIG. 1 is a perspective view of an intravenous pump set utilizing pumping apparatus.

FIG. 1 is an illustration of an intravenous administration set up using a pump and a source of intravenous fluid such as a flexible container. Pump 20, which is provided with a pump operating mechanism and operating electronics (not shown), is mounted on an I.V. stand 22 which also serves as a support for the intravenous fluid container 24. Container 24, which typically contains a fluid 26 such as saline that is continually administered, is also suspended from stand 22.

An administration set 10 provides a flow path from container 24 to the patient via pump 20. Set 10 includes a segment of flexible plastic tubing 26 such as polyvinyl chloride (PVC) tubing.

Tubing 26 at its proximal end is attached to a drip chamber 28 that in turn is attached via a spike (not shown) to an outlet port 30 of container 24. A clamping means such as a roller clamp 32 is positioned on tubing 26 at a point between pump 20 and container 24. Tubing 26 has connected at its distal end means for connecting set 10 to a vein access device, such as a catheter or needle (not shown).

Pump 20 includes a hinged door 36 which covers the peristaltic pumping apparatus hardware. To set up pump 20, door 36 is opened, tubing 26 is inserted into the peristaltic pumping apparatus as described in detail below, door 36 is closed, and pump 20 is activated. Pump 20 also defines apertures 38 at the upper and lower (not shown) peripheries of the door 36 through which the tubing 26 extends when door 36 is closed.

While the embodiment depicted in FIG. 1 includes a dual drive peristaltic pump, the present invention contemplates use of any number of pump drives in a single peristaltic pump.

Figure 2:
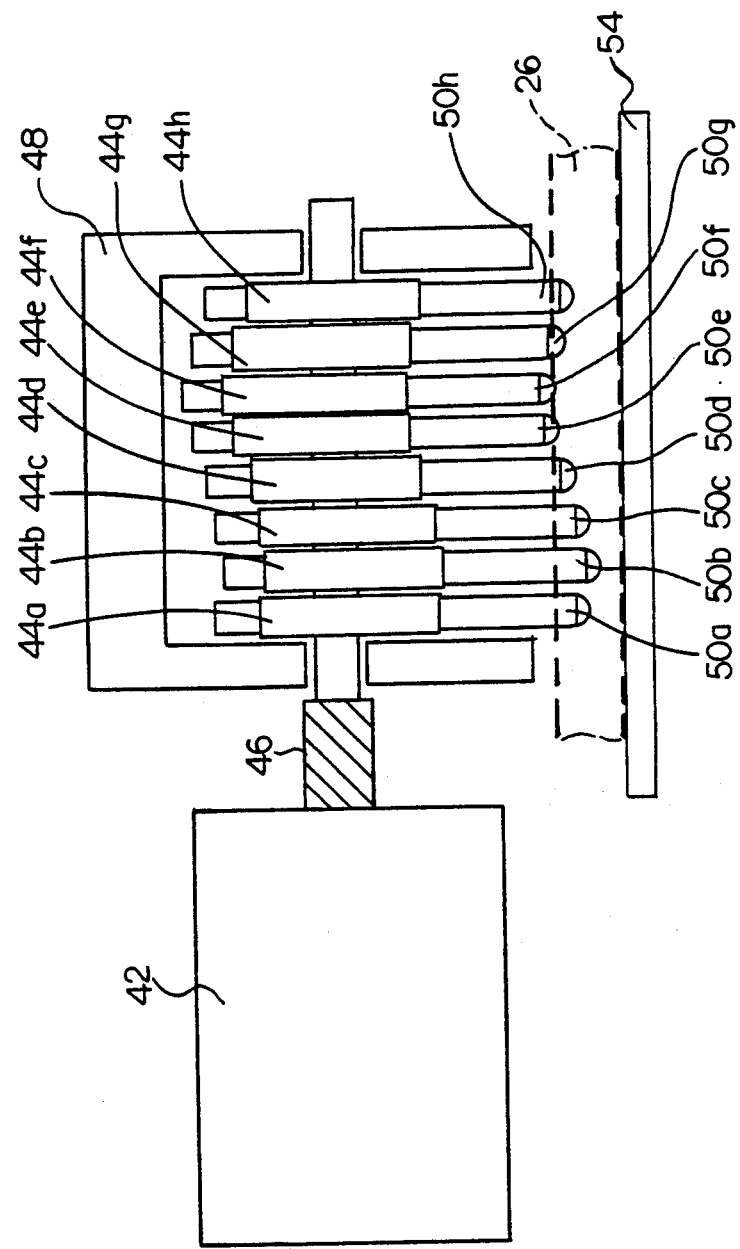
FIG. 2 is a general schematic of a peristaltic pumping apparatus.

Referring to FIG. 2, a general schematic of a peristaltic pumping apparatus is seen. A driving motor 42 is connected to a plurality of cams 44$a$-$h$ via a drive shaft 46. While in the embodiment depicted in FIG. 2 eight cams are utilized, any number of cams are contemplated in the present invention. Each cam 44 is angularly displaced from the adjacent cam. The plurality of angularly displaced cams 44$a$-$h$ are journaled in housing 48 which enables rotation in conjunction with the drive shaft 46.

A plurality of reciprocating pressure fingers 50$a$-$h$ are provided, the number of which corresponds to the number of cams 44. Each pressure finger 50 cooperates with a corresponding cam 44 by acting as a cam follower to reciprocally drive the pressure finger 50. The rotational movement of the drive shaft 46 is thus converted into a linear wave movement of the plurality of reciprocating pressure fingers 50$a$-$h$.

A pressure plate 54 is provided located juxtaposed to the pressure fingers 50$a$-$h$ and extending parallel to the axis of the cams. Tubing 26 is contained between the pressure fingers 50$a$-$h$ and the pressure plate 54. Fluid propulsion is effectuated by the pressure fingers 50$a$-$h$ squeezing the tubing 26 n the linear wave movement imparted by the angular orientation of the cams 44$a$-$h$.

Figure 4:
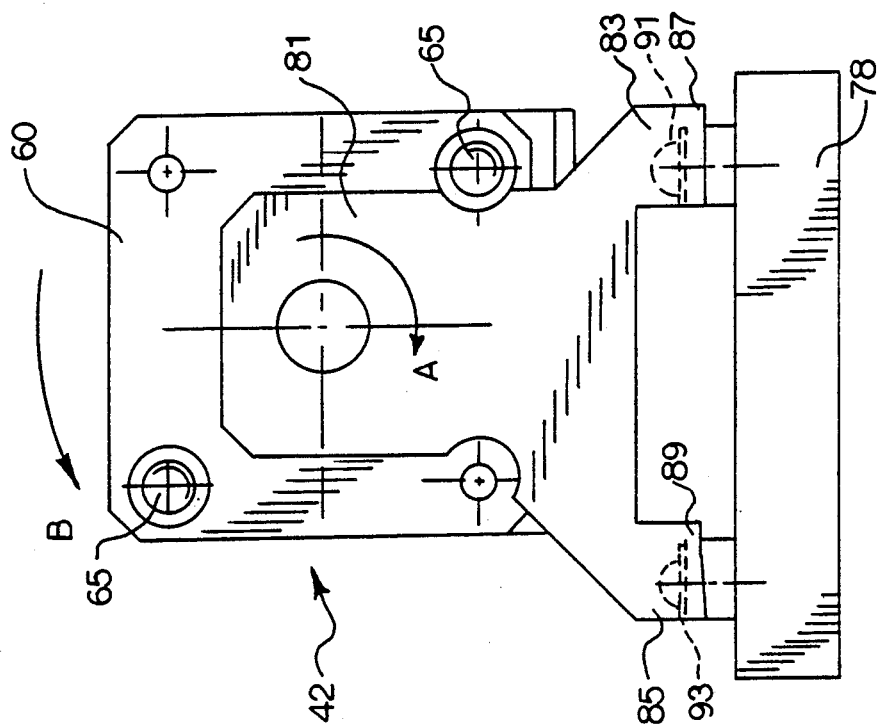
FIG. 4 is a back elevational view of the driving motor housing of FIG. 3.
Figure 3:
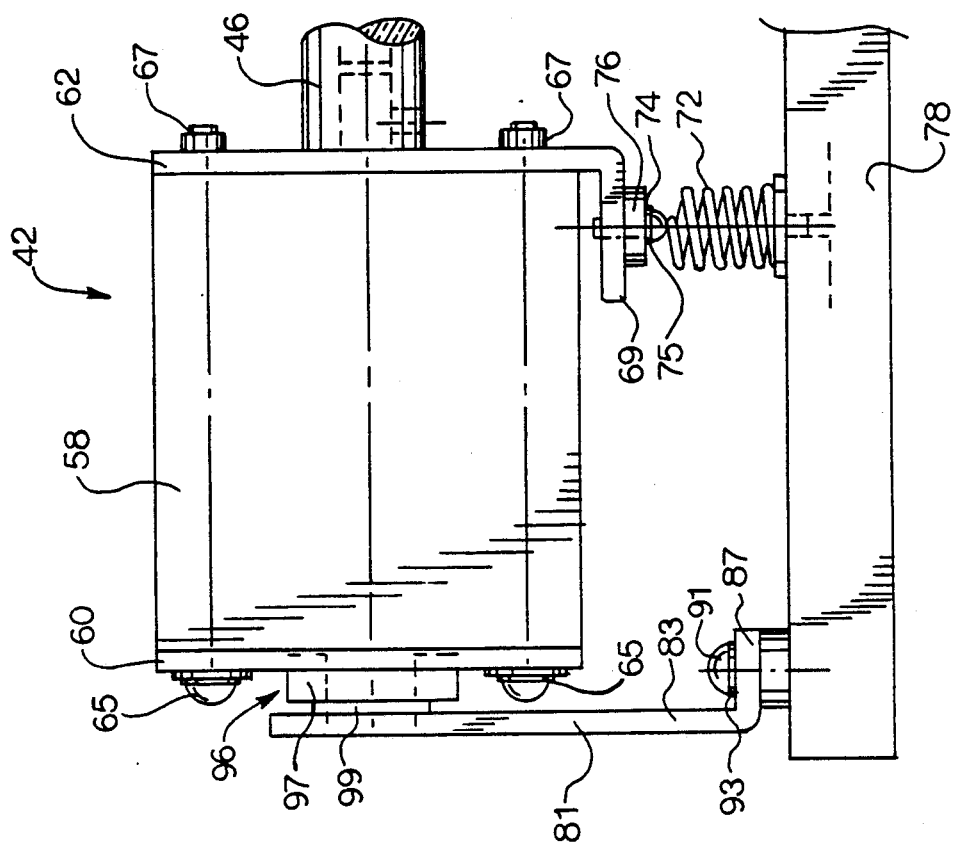
FIG. 3 is a side elevational view of driving motor housing in accordance with the principles of the present invention.

Referring now to FIGS. 3 and 4, a stepping motor 42 made in accordance with the principles of the present invention is seen. The stepping motor 42 includes stepping motor housing 58 which contains the operating elements of stepping motor 42. A distal end plate 60 is rigidly mounted to a face of stepping motor 42 opposite the drive shaft 46 while a proximal end plate 62 is rigidly mounted to a face of stepping motor 42 from which the drive shaft 46 extends. A pair of bolts 65 extend through apertures defined in distal end plate 60, through stepping motor housing 58, and through apertures defined in proximal end plate 62 to receive cooperating nuts 67 to rigidly secure the end plates 60,62 and the stepping motor housing 58.

Proximal end plate 62 extends downwardly from the proximal face of stepping motor housing 58 and includes an L-shaped portion 69. Proximal 62 end plate thus acts as a bracket securing the stepping motor housing 58. A biasing member which can include two springs 72 (partially cut away in FIG. 3) is secured to L-shaped portion 69 by fastening means such as a pilot 76 and bolt 74 extending through and secured to a threaded aperture defined in the L-shaped portion 69. A locking washer 75 is also utilized to maintain the bolt 74 secure in the presence of the stepping motor 42 vibrations. Springs 72 are similarly secured to a pump frame 78 by fastening means such as a pilot 80, a bolt 82 and a lock washer 84 (seen in FIG. 5).

A separate bracket 81 is provided distal to the stepping motor housing 58. The separate bracket 81 is securely mounted to pump frame 78 by two legs 83,85 which extend downwardly from bracket 81 and which include two L-shaped portions 87,89. The L-shaped portions 87,89 include an aperture through which a bolt 91 cooperating with a lock washer 93 secures each leg 83,85 to pump frame 78.

Secured to distal end plate 60 and separate bracket 81 is a bearing assembly 96. The bearing assembly 96 includes a first portion of bearing housing 97 rigidly secured to distal end plate 60 and a second cooperating portion of bearing housing 99 rigidly secured to the separate bracket 81. Use of the cooperating portions of bearing housing 97,99 in conjunction with ball bearings (not shown) results in distal end plate 60 of stepping motor 42 being rigidly secured against radial forces of stepping motor 42 while allowing free rotational movement about the axis of the drive shaft 46. As such, the bearing assembly 96 acts as means for allowing rotational movement of the stepping motor housing while rigidly securing against radial forces.

The stopping and starting of the stepping motor 42 results in tangential forces applied to the stepping motor housing 58 which urge movement of the stepping motor housing 58 in a rotational direction about the axis of the drive shaft 42. These tangential forces are all transferred to proximal end plate 62 as distal end plate 60 in conjunction with the bearing assembly 96 provides no resistance to these forces.

These tangential forces are in turn transferred to L-shaped portion 67 of distal end plate 62. To prevent these tangential forces from being transferred to pump frame 78, the biasing member acts as means for dampening these tangential forces.

Figure 5:
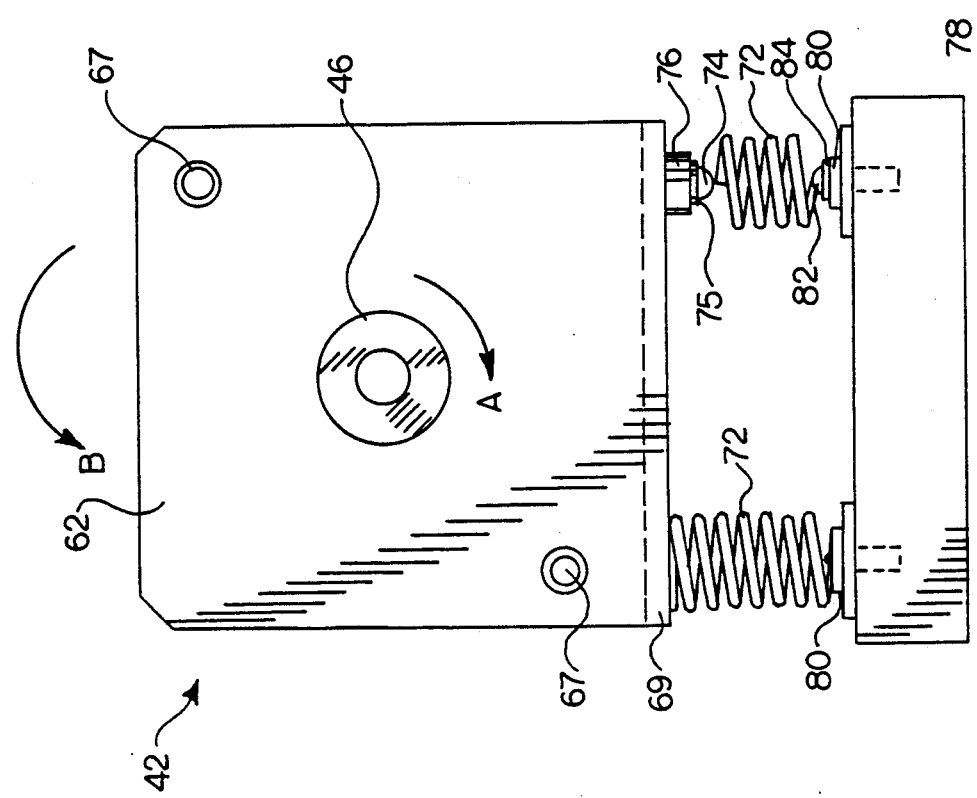
FIG. 5 is a front elevational view of the driving motor housing of FIG. 3.

Referring to FIG. 5, a preferred embodiment of the biasing member is seen. A pair of springs 72 are provided secured to L-shaped portion 69 of proximal end plate 62 and pump frame 78 by pilot 76, bolt 74 and locking washer 75. While in this preferred embodiment springs 72 are secured in a generally vertical orientation, the resiliency of the springs allows for dampening of tangential forces.

Figure 6:
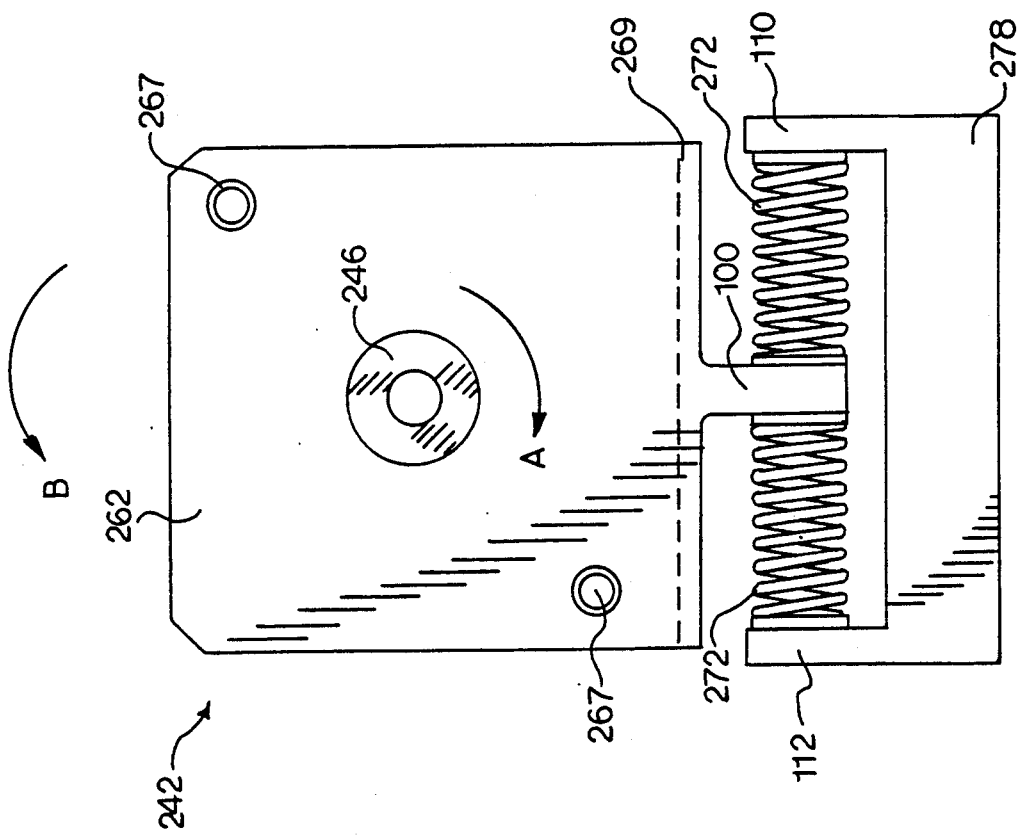
FIG. 6 is a front elevational view of an alternate preferred embodiment of the driving motor housing in accordance with the principles of the present invention.

Referring now to FIG. 6, an alternate preferred embodiment of the biasing member is seen in detail in which like elements are designated by the 200 series of like numerals. Biasing members again include a pair of springs 272 secured between proximal end plate 262 and pump frame 278. In this embodiment, L-shaped portion 269 includes a downwardly extending portion 100 to which the springs 272 are secured. Additionally, pump frame 278 includes a pair of upwardly extending members 110,112 which are horizontally displaced from downwardly extending portion 100 of L-shaped member 269. The springs 272 are secured between downwardly extending portion 100 of L-shaped member 269 and upwardly extending members 110,112, thereby assuming a generally horizontal orientation. In this orientation, the longitudinal axis of springs 272 extends in a direction tangential to the axis of rotation of the stepping motor 242. Thus, the tangential forces which result from the stopping and starting of the stepping motor 242 are applied to the springs 272 along the compression axis of the springs 272. It will be apparent to those skilled in the art that in either embodiment the springs can suitably be in extension or compression to gain the desired results.

In operation, at rest or in an equilibrium position between stepping increments, the stepping motor housing 58 is supported by the radially secured distal end plate 60 and the balanced compression springs 72. When a drive pulse is supplied to the drive shaft 46, the drive shaft 46 rotates in a forward direction, designated A in the figures, which drives the cams 44a–h and pressure fingers 50a–h to propel the fluid.

The driving force will also move the stepping motor housing 58 in a reactive opposite direction to movement of the drive shaft 46, designated B in the figures. This reactive movement will be much less than the movement of the drive shaft 46 due to the greater mass of the stepping motor housing 58, which results in a greater inertia than the drive shaft 46. Further, the bias of the compression springs 72 will both reduce the movement of the stepping motor housing 58 as well as absorb a portion of the tangential forces. Thus, the shock of the step movements is absorbed in the compression springs 72 which results in a reduction of these forces applied to the pump frame 78 to reduce the undesirable vibration and noise.

After the stepping motor 42 has completed the step increment and is at rest, the tangential force absorbed in the compression springs 72 is released which causes the stepping motor housing 58 to recover to the equilibrium position. This recovery drives the drive shaft 46 in the forward rotational direction the same distance that the stepping motor housing 58 moved. This ensures the accuracy of the pump 20 as the complete stepping motor movement is transferred to the pressure fingers 50a–h.

It should be understood that various changes and modifications to the preferred embodiments will be apparent to those skilled in the art. For example, the principles of the present invention can also apply to rotary-type peristaltic pumps. Such changes and modifications can be made without departing from the spirit and scope of the present invention and without diminishing its attendant advantages. It is, therefore, intended that such changes and modifications be covered by the appended claims.

What is claimed is:

1. A stepping motor apparatus comprising:
    a first bracket secured to a stepping motor, the first bracket being secured to a frame by means for dampening tangential forces; and
    a second bracket secured to the frame, the second bracket being secured to the stepping motor by means for allowing rotational movement of the stepping motor while rigidly securing against other forces.

2. The stepping motor of claim 1 wherein the means for allowing rotational movement of the stepping motor while rigidly securing against other forces includes a bearing assembly securing the stepping motor to the second bracket.

3. The stepping motor of claim 1 wherein the dampening means comprises a biasing member.

4. The stepping motor of claim 3 wherein the biasing member includes at least one spring.

5. The stepping motor of claim 4 wherein the spring is in compression.

6. The stepping motor of claim 4 wherein the spring is in extension.

7. The stepping motor of claim 4 wherein the spring includes a compression axis which is oriented tangentially from an axis of rotation off the stepping motor.

8. A peristaltic pump comprising:
    a driving motor contained in housing, the driving motor including a rotating drive shaft;
    a plurality of angularly displaced cams secured to the drive shaft;
    a plurality of cam followers cooperating with the cams, the cam followers including reciprocating pressure fingers;
    a first bracket secured to the driving motor housing and including means connected to a pump frame for dampening tangential forces; and
    a second bracket secured to the pump frame and including means connected to the driving motor housing for allowing rotational movement of the driving motor housing.

9. The peristaltic pump of claim 8 wherein the driving motor is a stepping motor.

10. The peristaltic pump of claim 8 wherein the means for allowing rotational movement of the stepping motor housing includes a bearing assembly securing the stepping motor housing to the second bracket.

11. The peristaltic pump of claim 8 wherein the dampening means comprises a biased member.

12. The peristaltic pump of claim 11 wherein the biased member includes at least one spring.

13. The peristaltic pump of claim 12 wherein the spring is in compression.

14. The peristaltic pump of claim 12 wherein the spring is in extension.

15. The peristaltic pump of claim 12 wherein the spring includes a compression axis which is oriented tangentially from the axis of rotation of the stepping motor.

* * * * *